(12) United States Patent
Hale (10) Patent No.: US 7,803,750 B2
(45) Date of Patent: Sep. 28, 2010

(54) METHOD OF MODULATING MELANIN PRODUCTION

(75) Inventor: Laura P. Hale, Hillsborough, NC (US)

(73) Assignee: Duke University, Durham, NC (US)

( * ) Notice: Subject to any disclaimer, the term of this patent is extended or adjusted under 35 U.S.C. 154(b) by 1858 days.

(21) Appl. No.: 10/627,966

(22) Filed: Jul. 28, 2003

(65) Prior Publication Data

US 2004/0241116 A1    Dec. 2, 2004

Related U.S. Application Data

(60) Provisional application No. 60/398,725, filed on Jul. 29, 2002.

(51) Int. Cl.
*A61K 38/00* (2006.01)
*C07K 14/00* (2006.01)
*C07K 14/435* (2006.01)

(52) U.S. Cl. .............................. 514/2; 514/21; 530/350

(58) Field of Classification Search ...................... 514/2
See application file for complete search history.

(56) References Cited

OTHER PUBLICATIONS

Freshney (Culture of Animal Cells, A Manual of Basic Technique, Alan R. Liss, Inc., 1983, New York, p. 4).*
Dermer (Bio/Technology, 1994, 12:320).*
Poortmans et al (J. Lab. Clin. Med., 1968,71:807-811).*
Lei et. al (Journal of Cellular Biochemistry, 1997, 67:216-222).*
Merriam Webster Online Dictionary (www.m-w.com/cgi-bin/dictionary?book=Dictionary&va=aberrant).*
Gura (Science, v278, 1997, pp. 1041-1042, IDS).*
Jiménez-Cervantes et al "Inhibition of melanogenesis in response to oxidative stress: transient downregulation of melanocyte differentiation markers and possible involvement of microphthalmia transcription factor", Journal of Cell Science 114:2335-2344 (2001).
Martinez-Esparza et al, "Transforming growth factor beta mediates hyoppigmentation of B16 mouse melanoma cells by inhibition of melanin formation and melanosome maturation", Int. J. Biochem. Cell Biol. 10:971-983 (200)—Abstract.

* cited by examiner

*Primary Examiner*—Peter J Reddig
(74) *Attorney, Agent, or Firm*—Nixon & Vanderhye P.C.

(57) ABSTRACT

The present invention relates, in general, to melanin production and, in particular, to a method of modulating melanin production and to compounds and compositions suitable for use in such a method.

4 Claims, 5 Drawing Sheets

Fig. 5D

METHOD OF MODULATING MELANIN PRODUCTION

This application claims priority from Provisional Application No. 60/398,725, filed Jul. 29, 2002, the content of which is incorporated herein by reference.

TECHNICAL FIELD

The present invention relates, in general, to melanin production and, in particular, to a method of modulating melanin production and to compounds and compositions suitable for use in such a method.

BACKGROUND

Zinc alpha-2-glycoprotein (ZAG) is a plasma glycoprotein that was named for its electrophoretic mobility and for its ability to be precipitated by Zn salts (Burgi and Schmid 1961). It is a member of the immunoglobulin gene superfamily and has a three-dimensional structure that is highly homologous to MHC class I and II molecules (Sanchez et al 1999). ZAG has been detected immunohistochemically in normal secretory epithelial cells of breast, prostate, and liver, in salivary, bronchial, gastrointestinal, and sweat glands (Tada et al 1991; Hale et al 2001), and in normal stratified epithelia including epidermis (Lei et al 1997; Brysk et al 1997b). ZAG mRNA is expressed in a similar distribution (Freije et al 1991). Consistent with its production by secretory epithelium, ZAG is present in most body secretions and constitutes 2.5% and 30% of the proteins present in saliva and seminal fluid respectively (Poortsmans and Schmid 1968). Plasma or serum levels of ZAG have been described to vary with age, with reported values ranging from 0.9-3.5 mg/dl (fetal) to 7.8-12.1 mg/dl (young adults) to 18-30 mg/dl (normal men aged 51-70)(Jirka et al 1974; Jirka et al 1978; Hale et al 2001). ZAG accumulates in breast cyst fluids to 30-50-fold plasma concentration (Bundred et al 1987; Sanchez et al 1997) and is over-expressed in 40-50% of breast carcinomas (Bundred et al 1987; Sanchez et al 1992; Diez-Itza et al 1993). It has recently been shown that ZAG is produced in high amounts by most prostate carcinomas, resulting in elevated serum levels of ZAG in prostate cancer patients (Hale et al 2001). ZAG has also been identified in epidermal malignancies, including squamous and Merkel cell carcinomas, with lesser expression in basal cell carcinomas (Brysk et al 1997b; Lei et al 1997). Little is known about mechanisms regulating ZAG expression by tumors, however ZAG production by normal epithelial tissues was shown to be increased by treatment with androgens, corticosteroids, interferon-α, or TGF-α (Lopez-Boado et al 1994; Brysk et al 1997; Brysk et al 1997b).

The normal functions of ZAG are unclear, however ZAG has been isolated from the urine of human cancer patients with cachexia and can function as a lipid-mobilizing factor. ZAG purified from human or mouse serum or human cancer patient urine induces lipolysis resulting in glycerol release and also increases lipid utilization in both human and mouse adipocytes (Hirai et al 1998). ZAG activates a GTP-dependent adenylate cyclase activity on adipocyte membranes, increasing cellular cAMP levels (Hirai et al 1998). This may potentially lead to activation of multiple cellular pathways, however further details of its mechanism of action are unknown. Using a panel of murine tumors, Todorov et al (1998) quantitated ZAG production in vitro and showed that cachexia induction in mice bearing these tumors in vivo correlated with their ZAG production. Whether ZAG has additional biological activities in addition to cachexia induction is unknown.

To further investigate biologic properties of ZAG, stable transfectants of recombinant human (rh)ZAG were created in the B16F10 murine melanoma cell line. The effect of ZAG transfection on melanin production was determined in vitro and in vivo. The effect of exogenous ZAG on melanin production by parent B16 cells and melan-A primary melanocytes was determined. Finally, the effect of ZAG on tyrosinase expression and activity was determined. Taken together, these studies show that ZAG inhibits melanin production in both normal and malignant melanocytes. Mechanisms include post-transcriptional effects on tyrosinase protein, with the potential for additional indirect effects. These studies resulted in the identification of a previously unknown biologic function of ZAG and have made possible a method of modulating melanin production and thereby preventing and/or decreasing pigmentation of skin and hair due to increased melanin production.

SUMMARY OF THE INVENTION

The present invention relates generally to melanin production. More specifically, the invention relates to a method of modulating melanin production. The invention further relates to compounds and compositions suitable for use in such a method.

Objects and advantages of the present invention will be clear from the description that follows.

BRIEF DESCRIPTION OF THE DRAWINGS

FIG. 1: B16-rhZAG clones demonstrate decreased melanin production in vitro. A. Visual inspection of media in stacked culture plates shows decreased melanin production by B16-rhZAG clones 10XA8 (lower plate) and 3G12 (middle plate) compared to B16-V cells (top plate) approximately 24 hours after achieving confluence. Eosin-stained cytocentrifuge preparations of B16-rhZAG clones 3G12 (C) and 10XA8 (D) also show decreased numbers of heavily melanized cells relative to B16-V cells (B) when examined during logarithmic growth.

FIG. 2. Decrease in melanin production by B16 cells in vitro correlates with ZAG over-expression. $5 \times 10^5$ cells were plated in 11 ml of phenol red-free media per 100 mm dish 96 hours prior to beginning absorbance measurements and reached confluence approximately 72 hours after plating. ZAG concentrations peaked at 47 hours post-confluence for 3G12 cells (A). Spectrophotometric analysis of culture supernatants (B) shows a significant lag in melanin production by B16-rhZAG clone 3G12, with peak $A_{600}$ at 58 hours post-confluence. Decreased melanin production by B16-rhZAG clone 10XA8 was not detectable at the time points analyzed in these experiments. Media appeared black visually when $A_{600}$ was $\geq 0.100$.

FIG. 4: ZAG over-expression decreases melanin synthesis in vivo through post-transcriptional effects on tyrosinase protein. A ferrous ion uptake stain shows abundant melanin production (blue color) in B16-V cells (A), with near total absence of reactivity in murine tumors derived from B16-rhZAG clone 3G12 (B). Incubation of frozen tumor sections with L-DOPA shows strong tyrosinase activity (black color) in B16-V tumors (C) compared to almost total lack of tyrosinase activity in B16-rhZAG tumors (D). Immunoperoxidase staining with αPEP7 antiserum specific for tyrosinase showed decreased reactivity (red color) with B16-rhZAG tumors (F) relative to B16-V tumors (E). No staining is seen in B16-V (G) or B16-rhZAG (H) tumors using normal rabbit serum as a negative control.

FIG. 5: Exogenous ZAG inhibits melanin production by melan-A primary melanocytes in vitro. The indicated amount of ZAG was added to 6 well plates seeded with $0.165 \times 10^6$ melanA cells and cultured for 96 hours prior to harvesting the cells for assessment of melanin production by absorbance at 600 mm, histologic examination, and Western blot. A. ZAG inhibited melanin production in a dose-dependent fashion as determined by absorbance measurements of cell lysates. Data shown is the mean±range of 2 independent experiments. Three additional experiments that used differing numbers of cells and different ZAG concentrations also showed a dose-dependent inhibition of melanin production. B. A Western blot detected with αPEP7 anti-tyrosinase antiserum demonstrates that tyrosinase protein is decreased in melan-A cells treated with 150 mg/ml ZAG as compared with PBS-treated control cells. C, D. Eosin-stained cytocentrifuge preparations show decreased numbers of heavily melanized cells in ZAG-treated (150 µg/ml)(panel D) vs. control melan-A cultures (panel C).

DETAILED DESCRIPTION OF THE INVENTION

Problems with increased or aberrant skin pigmentation can be psychologically devastating when widespread. Such changes may still cause significant distress even when localized to small area of the skin, especially when aberrant pigmentation involves the face and/or hands. The color of skin and hair depends on the amount of eumelanin that it contains. Eumelanin is produced by melanocytes through a series of chemical reactions that are regulated by the enzyme tyrosinase.

The present invention results from studies demonstrating that ZAG can inhibit melanin production by melanocytes. Increased levels of ZAG supplied as purified protein or through transfection and endogenous expression decreases the levels of tyrosinase protein and appear to decrease the activity of any residual tyrosinase enzyme. Application of ZAG to normal melanocytes in vitro results in marked decreases in melanin synthesis by these cells.

The present invention thus relates to a method of inhibiting melanin synthesis. The present method is useful in clinical situations of hyperpigmentation due, for example, to sun-exposure, inflammation, or scarring or to disorders with congenital or acquired proliferations of melanocytes. ZAG is produced by epidermal keratinocytes, thus it can be applied locally to the epidermis as well as systemically.

Decreases in skin and hair pigmentation due to aging begin with decreased melanin synthesis by existing melanocytes. ZAG concentrations in human blood increase substantially with age (Hale et al, Clin. Can. Res. 7:846 (2001)). Interfering with the action of ZAG locally on melanocytes can be used in a method of preventing age-related loss of hair and skin pigmentation. Furthermore, inhibition of naturally produced ZAG can allow restoration of pigmentation in skin and hair to decrease susceptibility to UV-induced cancers and to reverse age-related changes in hair and skin color.

ZAG decreases melanin synthesis by decreasing the amount and activity of tyrosinase in both normal and malignant melanocytes. Tyrosinase is a tumor-associated antigen in melanoma that has been investigated as a target for immunotherapy. Modulation of tyrosinase protein levels by ZAG can be useful in enhancing the efficacy of immunotherapy targeting tyrosinase.

ZAG can be formulated as a composition using any of a variety of physiologically acceptable carriers, excipients or diluants. The compostion can be, for example, in a cream, gel or lotion for topical use or can be present as a liquid, e.g., a sterile liquid when used systemically. The composition can also be present in dosage unit form, e.g., as a tablet or capsule.

The data presented in the Example that follows show that ZAG regulates melanin production in B16 melanoma cells, a widely used model of melanocyte function. The generalizability of the anti-melanogenic functions of ZAG is further demonstrated by its inhibitory effect on melanogenesis by melan-A normal murine melanocytes in vitro. ZAG is produced by normal epidermal keratinocytes, where its expression increases with cellular differentiation (Lei et al 1997). Others have previously demonstrated that keratinocyte-derived factors influence melanocyte behavior, including melanocyte proliferation, dendricity, and total melanin production (Gordon et al 1989). Thus taken together, the data provided herein indicate that epidermal-derived ZAG plays a role in normal regulation of melanin production in vivo, in addition to its previously described role in cancer cachexia.

The studies described in the Example that follows demonstrate that B16 tumor cells that are either transfected to strongly express ZAG or treated with exogenous ZAG have decreased melanin production in vitro. B16 tumors strongly expressing ZAG also have decreased growth and form amelanotic tumors in vivo. Despite qualitatively similar levels of tyrosinase mRNA expression, ZAG-transfected B16 (B16-rhZAG) tumors had decreased levels of tyrosinase protein and minimal tyrosinase activity. Purified ZAG also decreased melanin production by B16-V cells in vitro and decreased tyrosinase activity in B16-V tumor sections in vitro. Taken together, these results demonstrate that ZAG inhibits melanin synthesis in B16 cells at a post-transcriptional level. However, ZAG appears to decrease tumor cell growth and melanin synthesis in vivo more strongly relative to its effects in vitro, indicating that ZAG may also act through other indirect mechanisms in vivo. ZAG similarly decreases melanin production in primary murine melanocytes in vitro.

Figure 1A:
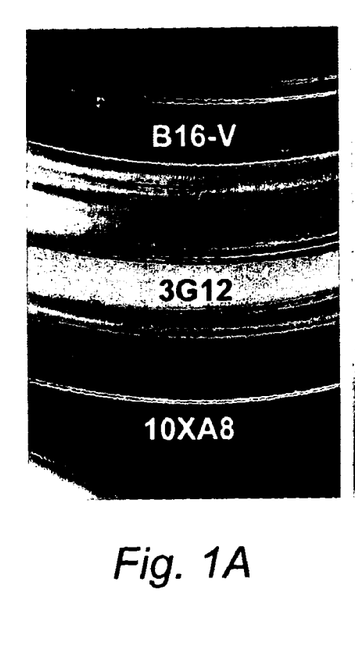
Figure 1B:
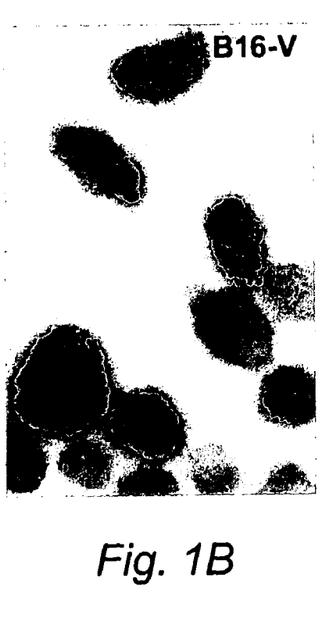
Figure 1C:
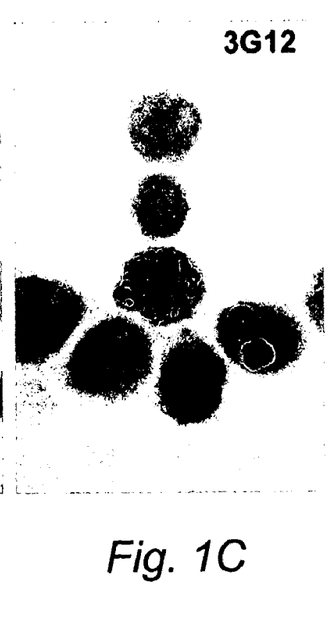
Figure 1D:
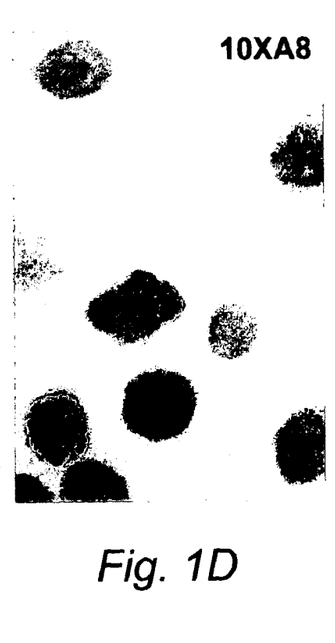
Figure 2A:
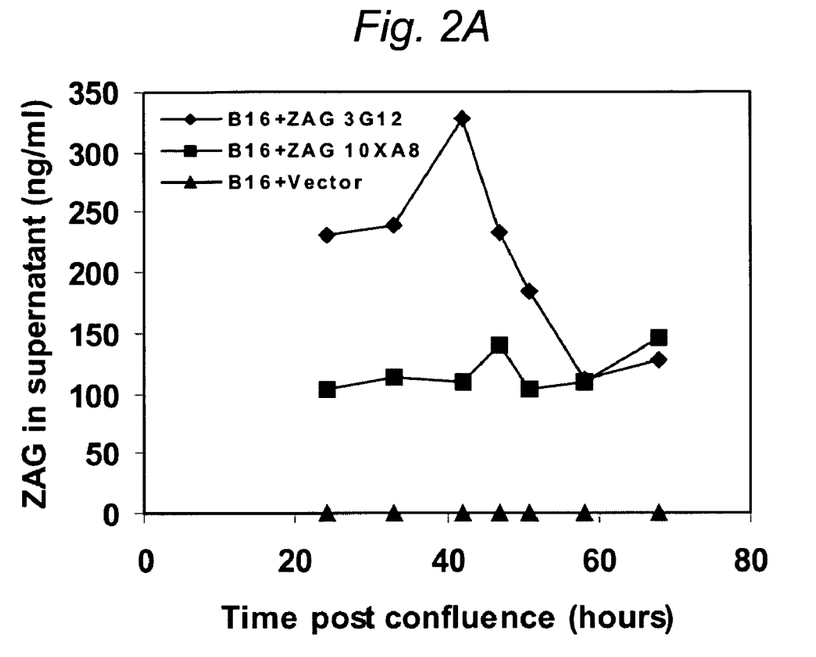
Figure 2B:
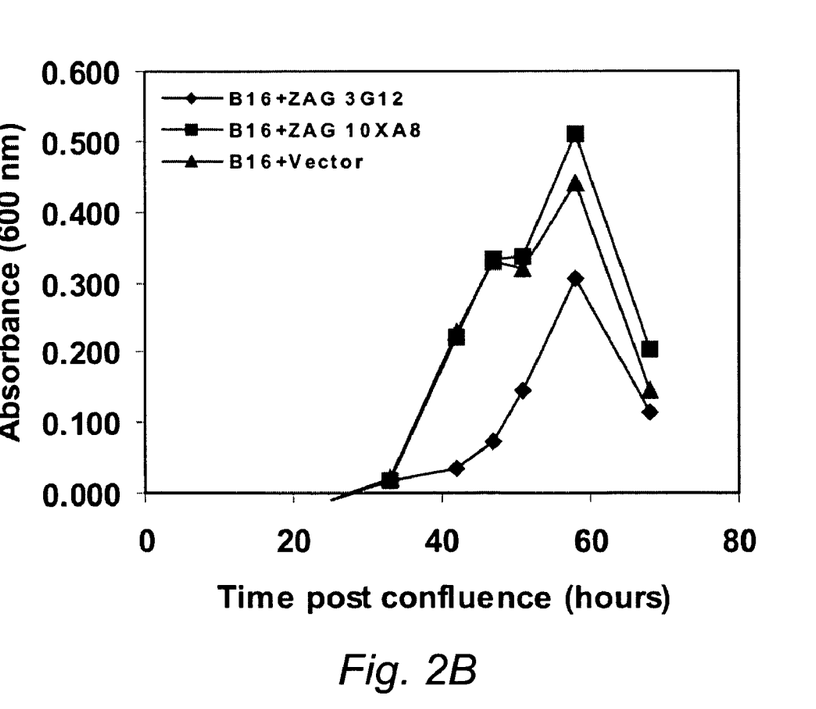

Moderate to high levels of ZAG are required to achieve significant inhibition of melanin synthesis. B16 cells are normally highly melanized despite their production of low levels of murine ZAG (Todorov et al 1998). The numbers of heavily melanized cells are decreased similarly in ZAG-transfected 10XA8 and 3G12 cultures (FIGS. 1C,D). However the accumulation of melanin in the media decreases much more in 3G12 cultures that produce approximately twice the ZAG produced by 10XA8 cultures (FIGS. 1A, 2A, 2B). Indeed, although visual decreases in secretion of melanin into the media by 10AX8 can be observed at some time points compared with vector-transfected cells (FIG. 1A), secretion of melanin as measured by $A_{600}$ of media at other timepoints is not significantly decreased in 10XA8 (FIG. 2B). These observations may indicate that a threshold amount of ZAG may be required for simultaneously decreasing both melanogenesis and melanin secretion. However, the observation that ZAG-transfected tumor cells that make melanin in vitro are amelanotic in vivo (FIG. 4B) demonstrates that the concentration of ZAG required to inhibit melanin synthesis is readily achieved at tumor sites in vivo. A variety of tumor types derived from secretory and stratified epithelium, including squamous cell carcinomas, have been shown to produce measurable amounts of ZAG (Hale et al 2001; Lei et al 1997; Lei et al 1999; Bundred et al 1987; Sanchez et al 1992; Diez-Itza et al 1993). It has previously been shown that tumor-produced ZAG can contribute to elevated systemic (serum) ZAG levels in prostate cancer patients (Hale et al 2001).

Higher levels of exogenous rhZAG are required to achieve similar levels of tyrosinase inhibition when compared to ZAG production by rhZAG-transfected cells. This may reflect very high local concentrations adjacent to rhZAG-producing cells or may indicate that ZAG also affects tyrosinase activity through indirect mechanisms that require metabolism or changes in gene expression, protein synthesis or half-life of ZAG or other proteins. The in vivo studies that show essentially complete inhibition of melanogenesis in tumors of ZAG-transfected B16 cells in vivo compared with only partial inhibition in vitro also suggest that ZAG may inhibit melanin synthesis by indirect mechanisms. This may occur through effects on other cells that are present in vivo in addition to direct effects that ZAG has on the tumor cells themselves in vitro. Alternatively, in vivo growth conditions may have generated and selected for new tumor cell clones with resistance to ZAG and reduced production of melanin by alternative mechanisms.

The data presented show that ZAG expression also inhibits the growth of B16-rhZAG tumors in vivo. ZAG has previously been shown to inhibit the proliferation of the Tu-138 oral squamous cell carcinoma cell line, when the cells are plated directly onto immobilized ZAG (Lei et al 1999). This implies that ZAG has additional biologic effects on tumor cells beyond stimulating lipolysis and melanin synthesis.

α-melanocyte stimulating hormone (α-MSH) has previously been shown to regulate the expression of tyrosinase mRNA, in addition to having other neuroimmunomodulatory effects (Lipton and Catania 1997; Ottaviani et al 1997). While α-MSH was not measured directly, the studies presented in the Example provide no evidence for ZAG-induced changes in tyrosinase gene transcription. They do show a clear and direct effect of ZAG on level and activity of tyrosinase protein. However, decreased melanin synthesis by melanoma tumor cells could potentially arise from inhibition in multiple pathways. ZAG may influence melanin production by B16 melanoma cells by additional mechanisms in addition to effects on tyrosinase protein.

Since TNF-α has previously been shown to inhibit melanin synthesis by human primary melanoma and B16 melanoma cells (Swope et al 1991; Martinez-Esparza et al 1998; Martinez-Esparza et al 1999), it was important to determine whether ZAG acted via a mechanism involving TNF-α. TNF-α was undetectable in the supernatant of both B16-V and B16-rhZAG cells cultured in vitro and TNF-α mRNA could not be detected in either B16-V or B16-rhZAG cells by RT-PCR (data not shown). However, small amounts of TNF-α "spiked" into the supernatant from B16-V and B16-rhZAG cells could be detected quantitatively, indicating that these supernatants do not contain substances that interfere with detection of TNF-α protein. These findings indicate that ZAG inhibits melanin synthesis by B16 cells via a TNF-α-independent mechanism. ZAG may, however, be a TNF-mimetic or ZAG- and TNF-α-dependent pathways may share downsteam effector pathways.

Certain aspects of the invention can be described in greater detail in the non-limiting Example that follows.

EXAMPLE

Materials and Methods

Construction of ZAG-Producing Murine Cell Lines

A full-length human ZAG cDNA including the endogenous secretory signal sequence was cloned from human liver using RT-PCR and primers corresponding to bp 3-21 and bp 938-920 (GenBank D90427). The construct sequence was verified by automated DNA sequencing. Full length human ZAG cDNA was inserted into the pCDNA3.1 (−) Myc-His eukaryotic expression vector (Invitrogen, Carlsbad, Calif.) using restriction enzyme digestion and adapter ligation to ensure in-frame insertion relative to the myc and 6-His 3' epitope tags. Epitope-tagged recombinant human ZAG constructs were transfected into B16F10 (B16) murine melanoma cells (American Type Culture Collection, Rockville, Md.). Stable transfectants were obtained by G418 selection then cloned by limited dilution. Parent and transfected cell lines were grown in DMEM+10% fetal bovine serum at 37° C. in an atmosphere supplemented with 5% $CO_2$. Culture supernatants were analyzed in triplicate for expression of ZAG by antigen capture ELISA using anti-ZAG mAb 1B5 (Sanchez et al 1997) as capture antibody. Bound rhZAG was detected using biotinylated anti-ZAG mAb 1H4 (Sanchez et al 1997), streptavidin-horseradish peroxidase conjugate (Jackson ImmunoResearch Labs, West Grove, Pa.), and 3,3',5,5'-tetramethyl-benzidine substrate (Kirkegaard and Perry Laboratories, Gaithersburg, Md.). Standard curves were constructed using HPLC purified rhZAG, quantitated by $A_{280}$ (Burgi and Schmid 1961). The sensitivity of the assay was 10 pg/ml. ELISA results were confirmed by SDS-PAGE and Western blot detection of epitope-tagged recombinant human (rh) ZAG with the predicted molecular weight of 46 kDa using anti-ZAG mAb 1B5 and/or the India His-Probe™ nickel-horseradish peroxidase reagent (Pierce, Rockford, Ill.) specific for the 6-His epitope tag. Vector-transfected cell populations (B16-V) were also derived and used as controls. B16-V cells showed no evidence of reactivity with the anti-human ZAG mAbs used in either antigen capture enzyme immunoassays or Western blots (FIG. 1), although B16 cells have been shown to express small amounts of murine ZAG (Todorov et al 1998).

Analysis of Melanin Production

Melanin content of B16 cell lines was determined by microscopic evaluation of eosin-stained cytocentrifuge preparations. To be considered heavily melanized, cells had to contain >10 melanosome specks visible at a magnification of ×100 or ≧1 macro-melanosome. The majority of cells considered heavily melanized had at least a "salt and pepper" appearance with many melanosome specks present. Melanin production by B16 cell lines was also determined by absorbance measurements (600 nm) of phenol red-free culture supernatants.

Melan-A primary murine melanocytes (from Dr. Vincent Hearing, National Institutes of Health) were propagated in RPMI1640, 10% fetal bovine serum, 2 mM glutamine, 100,000 U/L penicillin, 100 mg/L streptomycin sulfate, 200 nM tetradecanoyl phorbol acetate and seeded into 6-well plates for measurements of melanin production. After 96 hours of culture with various concentrations of ZAG, media was aspirated and cells were washed once in PBS, then solubilized in 200 µl 1M NaOH, and pipetted repeatedly to homogenize. Melanin absorbance was determined at 600 nm. Melanin content of melan-A cells was also determined by microscopic evaluation of eosin-stained cytocentrifuge preparations.

Animal and Tissue Studies $2 \times 10^5$ rhZAG or vector-transfected B16 tumor cells were implanted subcutaneously in the flank in groups of 5 syngeneic female C57BL/6 mice. Mice were weighed then sacrificed and serum was obtained at 21 days post-implantation, just prior to tumor-related death. Tumor size was measured using calipers. The concentration of tumor-produced human ZAG in the serum was measured by antigen capture ELISA as described above. Each serum sample was analyzed in quadruplicate for at least 2 independent dilutions and results were averaged. Samples of tumors for histologic analysis were snap-frozen in Tissue-Tek OCT compound (Sakura, Torrance, Calif.) and stored at −80° C.

Immunoperoxidase staining for tyrosinase protein was performed on frozen sections of B16 tumors using αPEP7 rabbit polyclonal antiserum (gift of Dr. Vincent J. Hearing)(Jimenez 1991; Aroca 1993). Other reagents included biotinylated goat anti-rabbit secondary antibody, avidin-biotin-horseradish peroxidase complexes (VectaStainABC; Vector Laboratories, Burlingame, Calif.) and Nova Red substrate (Vector Laboratories). Negative controls to ensure the specificity of staining included use of normal rabbit serum on B16 tumors and use of αPEP7 on 4T1 murine breast carcinoma tumors that do not produce melanin.

Ferrous ion uptake and L-DOPA histochemical stains were performed on frozen sections of B16 tumors as described (Sheehan and Hrapchak 1987). The ferrous-ion uptake stain is specific for pre-formed melanin, generating a blue color in proportion to the amount of melanin present. The L-DOPA stain provides an assay for tyrosinase activity. In vivo, tyrosinase catalyzes the oxidation of tyrosine to DOPA (3,4-dihydroxyphenylalanine) as well as the oxidation of DOPA to melanin through intermediate steps. When fresh frozen tissue sections are incubated with a buffered solution of DOPA, a melanin-like pigment is deposited in proportion to the degree of tyrosinase activity present (Sheehan and Hrapchak 1987). A Nuclear Fast Red counterstain was used for both ferrous ion uptake and L-DOPA histochemical stains.

For Western blot determination of tyrosinase protein levels, protein extracts were prepared from five 20 μm frozen sections of B16-V or B16-rhZAG tumors or from cultured melan-A cells using 10 mM Tris pH 8.0, 150 mM NaCl, 1% Triton X-100, with protease inhibitors (Complete Mini EDTA-free Protease Inhibitor tablets, Roche Molecular Biochemicals, Indianapolis, Ind.). The protein content of tumor extracts was determined using the BCA™ assay (Pierce). Equal amounts of protein by weight for tumor extracts or corresponding to equivalent numbers of cells for melan-A cells were analyzed by SDS-PAGE, transferred to nitrocellulose, and reacted with αPEP7 anti-tyrosinase rabbit polyclonal antiserum or control rabbit serum followed by goat anti-rabbit immunoglobulin coupled to horseradish peroxidase. Bound antibody was detected by chemiluminescence (SuperSignal West Pico Chemiluminescence Substrate, Pierce).

RNA was isolated from tumor tissue using an RNeasy™ kit (Qiagen, Valencia, Calif.). Two μg of RNA was reversed transcribed using SuperScript (Gibco BRL, Rockville, Md.) and the resulting cDNA was subjected to PCR for 15, 20, 25, and 30 cycles using Platinum Taq (Gibco BRL). Primers were selected to cross intron-exon boundaries and did not amplify genomic DNA. Primer sequences for tyrosinase (415 bp) were 5' CAG ATC TCT GAT GGC CAT 3' (SEQ ID NO:1) and 5' GGA TGA CAT AGA CTG AGC 3' (SEQ ID NO:2)(bp 101-118 and bp 515-498, GenBank NM_011661) and for GAPDH (214 bp) were 5' TCG TCC CGT AGA CAA AAT G 3' (SEQ ID NO:3) and 5' TGA CAA GCT TCC CAT TCT C 3' (SEQ ID NO:4)(bp 31-49 and by 244-227, GenBank M32599). Products were analyzed on ethidium-bromide stained gels and ZAG to GAPDH product ratio was determined at 15, 20, 25, and 30 cycles for each sample.

Purification of ZAG rhZAG was purified from supernatant of rhZAG-transfected 293 human kidney epithelial cells using a Ni-NTA affinity column (Qiagen) specific for the His epitope tag or by concentration from serum free media (293 SFM II™, Gibco BRL) using a 30 kDa MW cutoff filter. SDS-PAGE gels followed by Western blotting confirmed that the protein in these ZAG preparations was highly immunoreactive with anti-ZAG mAb.

TNF-α Assays

TNF-α protein was detected by antigen capture enzyme immunoassay using the Duo-Set TNF-α kit (R&D Systems, Minneapolis, MN) according to the manufacturer's protocol. The sensitivity of this assay is 15 pg/ml. TNF-α mRNA was detected by RT-PCR assays using primers corresponding to by 301-318 and by 527-510 of the GenBank NM_013693 sequence (5' TGT CTA CTG AAC TTC GGG 3' (SEQ ID NO:5) and 5' TCT TTG AGA TCC ATG CCG 3', (SEQ ID NO:6) respectively). The 560 murine astrocytoma cell line transfected with TNF-α (Sampson et al 1997) was used as a control to insure appropriate detection of both TNF-α mRNA and protein under the conditions used.

Results

ZAG Over-Production Decreases Melanin Production by B16 Cells in vitro

In vitro, B16 melanoma cells typically produce melanin such that the culture supernatant turns visually black soon after cultures become confluent. Melanin production by B16-rhZAG clones 3G12 and 10XA8 that expressed ZAG at high levels was compared with that by B16-V cells. A clear and consistent decrease in the rate of melanin accumulation could be seen within cultures of B16-rhZAG vs. B16-V cells by visual inspection of media soon after cultures reached confluence (FIG. 1A). These visual differences could no longer be discerned at later timepoints when melanin accumulation was maximal (not shown). Eosin-stained cytocentrifuge preparations of B16-rhZAG clones 3G12 and 10XA8 and B16-V cells obtained from logarithmically growing cultures were also examined for the presence of the cytoplasmic dark specks that are indicative of melanin production. The amount of melanin present within the cytoplasm of ZAG-transfected cells was significantly decreased when compared with vector-transfected cells (FIG. 1B-D). Fewer B16-rhZAG cells contained visible melanin specks and less total melanin was present in the cytoplasm of B16-rhZAG cells that contained melanin specks. In particular, percentage of heavily melanized cells was significantly reduced in both B16-rhZAG clones analyzed relative to B16-V cells (16±1% and 14±2%, mean±SD respectively for 3G12 and 10XA8 vs. 45±2% for B16-V; $p<0.0003$). Thus high level expression of ZAG decreases melanin synthesis by individual B16-rhZAG cells.

ZAG Over-Expression Decreases the Rate of Melanin Accumulation in vitro

To further investigate the effects of ZAG over-expression on melanin accumulation during culture, serial measurements of both melanin and rhZAG present in the media from B16-rhZAG clones 3G12 and 10XA8 and B16-V cells were performed as a function of time. As shown in FIG. 2A, the concentration of ZAG peaks at 47 hours post-confluence and decreases thereafter. Although 3G12 cells produce melanin in vitro, cultures do not turn visibly black until 51 hours post-confluence, compared with 42 hours for 10XA8 and B16-V cells. Melanin accumulation in the media of the 3G12 cell line remains consistently below that of B16-V cells for all time points analyzed (FIG. 2B). Decreases in melanin production by B16-rhZAG clone 10XA8 compared with B16-V cells were not detectable at the time points analyzed in these experiments. Whether the increasing black color of the media from 24-58 hours post-confluence results from increased melanin synthesis and/or from increased secretion of melanin into the culture medium is unknown. Eosin-stained cytocentrifuge preparations of 3G12, 10XA8, and B16-V cells made 68 hours post-confluence show relatively few melanin granules compared with those made from logarithmically growing cells, suggesting that melanin secretion may increase post-confluence. However, these cells are viable and proliferate and synthesize melanin when passaged. The $A_{600}$ of the melanin-containing media decreases by the 68 hour point (FIG. 2B), most likely as a result of further oxidation or breakdown of previously produced melanin. This decreased absorbance suggests that oxidized melanin and/or melanin breakdown products contribute less to the measured $A_{600}$ as compared to newly synthesized or secreted melanin. The observation that the $A_{600}$ of melanin-containing media from B16-V cultures decreases during cell-free culture at 37° C. support this interpretation.

Exogenous ZAG Decreases Melanin Synthesis by B16-V Cells in vitro

Figure 3:
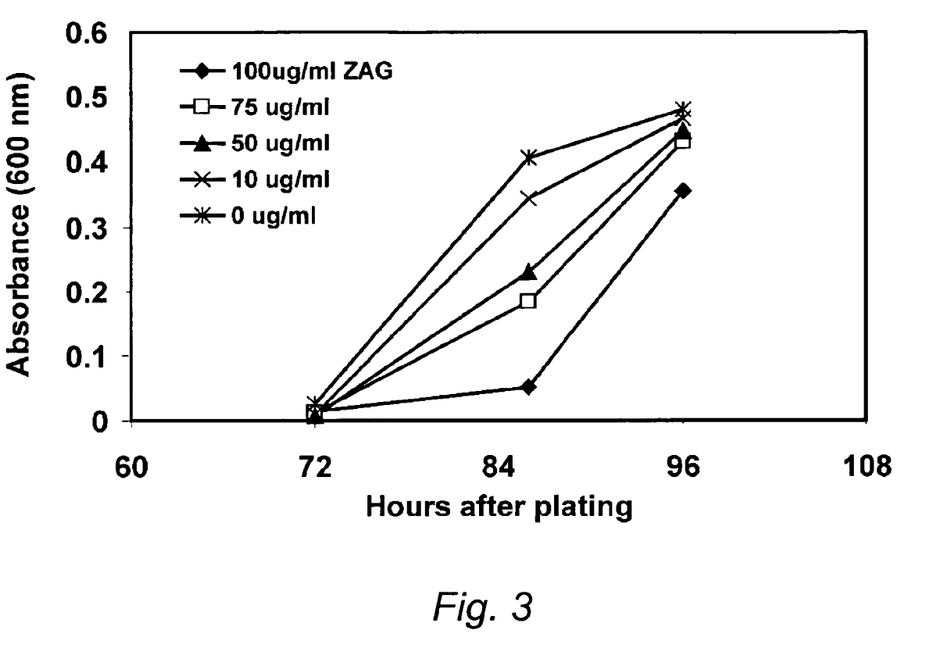
FIG. 3: Exogenous ZAG decreases melanin synthesis by B16-V cells in vitro. 10-100 µg/ml exogenous rhZAG inhibits the production and/or secretion of melanin into culture supernatant by B16-V cells. Results shown are representative of four experiments performed.

The above studies indicate that ZAG over-production is sufficient to decrease melanin synthesis by B16-rhZAG melanoma cells that are genetically engineered to over-express ZAG. To determine whether similar effects could be obtained when ZAG is supplied exogenously, B16-V cells were treated with purified rhZAG at concentrations ranging from 10-100 μg/ml. As shown in FIG. 3, addition of exogenous rhZAG also inhibited melanin production by B16-V cells in vitro in a dose-dependent fashion.

ZAG Expression Turns Off Melanin Synthesis by B16 Tumor Cells in vivo.

Figure 4A:
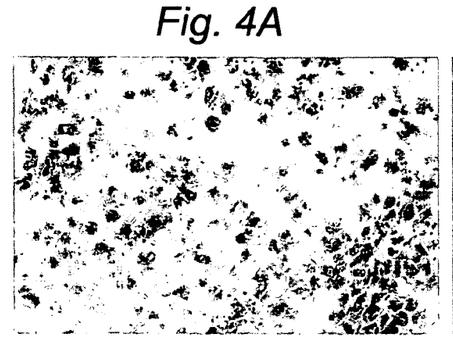
Figure 4B:
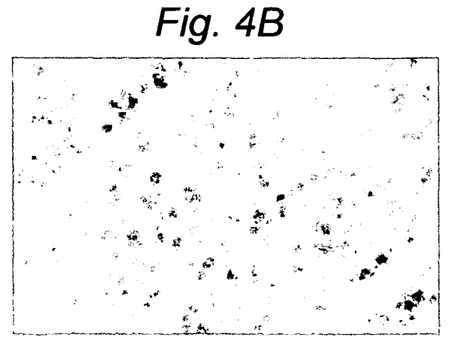

In addition to producing melanin in culture, B16 cells also typically produce melanin in vivo and B16 tumors thus appear black when grown in mice. The growth and melanin production by B16-rhZAG clone 3G12 and B16-V cells in vivo were next compared in groups of 5 syngeneic mice. B16-rhZAG tumors showed significantly decreased growth at 21 days compared with B16-V tumors (mean tumor volume±SEM: 289±74 mm$^3$ vs. 943±62 mm$^3$, p<0.0002). rhZAG could be detected in the serum of mice with B16-rhZAG but not B16-V tumors (156±70 ng/ml (mean±SD) vs. undetectable). Increased ZAG production by B16-rhZAG tumors was sufficient to cause a mean weight loss of 15% in the group bearing rhZAG-transfected tumors (ending weights: B16-vector 20.6±1.1 g; B16-ZAG 17.5±0.8 g; p=0.001) which remained significant when corrected for differences in tumor volumes. However, although B16-rhZAG clone 3G12 can produce (albeit decreased amounts of) melanin in vitro, tumors derived from these cells show no evidence of melanin production in vivo and thus appear white grossly. Histochemical staining using the more sensitive ferrous ion uptake stain similarly shows almost total lack of melanin production in B16-rhZAG tumors, as indicated by lack of blue reaction product (FIG. 4A,B). This marked decrease in melanin production by B16-rhZAG cells in vivo contrasts with the comparatively modest decrease in melanin production seen in these cells in vitro.

ZAG Affects Tyrosinase Activity at a Post-Transcriptional Level

Melanin synthesis is controlled in part by regulating the levels and/or activity of the tyrosinase enzyme that is required for the final stages of melanin synthesis. To further investigate mechanism by which tumor-produced ZAG affects melanin synthesis, the presence of mRNAs encoding tyrosinase in B16-rhZAG and B16-V cells grown in vitro and tumors grown in vivo were analyzed by RT-PCR. The amount of tyrosinase product relative to GAPDH product was similar in melanin-producing B16-V tumors vs. amelanotic B16-rhZAG tumors grown in vivo as well as in B16-rhZAG vs. B16-V cells grown in vitro. This suggests that the decrease in melanin production by ZAG-transfected B16 cells most likely occurs by a mechanism other than by transcriptional inhibition of tyrosinase mRNA production.

Figure 4C:
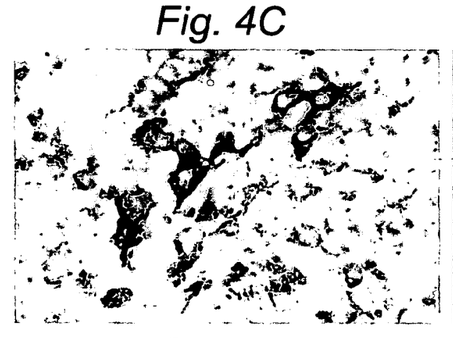
Figure 4D:
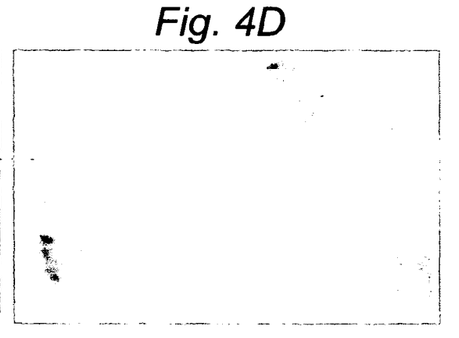
Figure 4E:
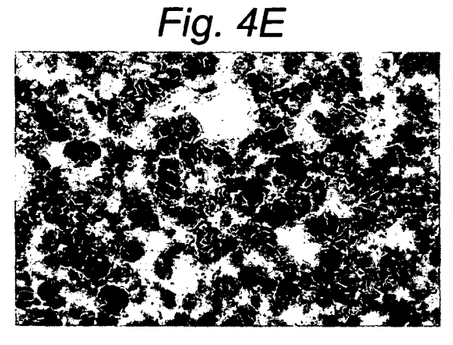
Figure 4F:
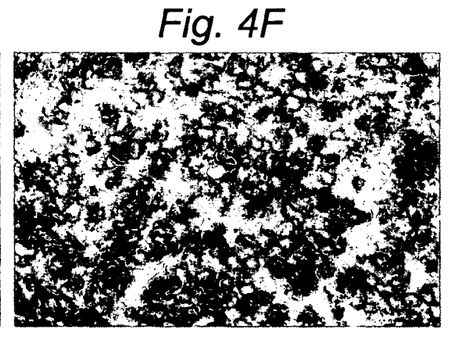
Figure 4G:
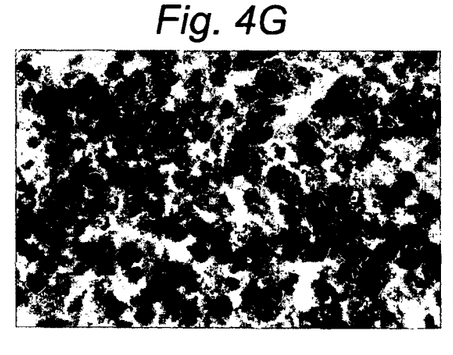
Figure 4H:
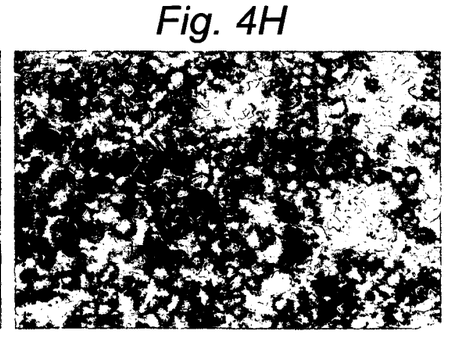

To determine how ZAG affects tyrosinase enzyme activity, frozen sections of B16-rhZAG and B16-V tumors were incubated with the tyrosinase substrate L-DOPA. Although strong tyrosinase activity can be observed in B16-V tumors (black color, FIG. 4C), very little tyrosinase activity is present in B16-rhZAG tumors (FIG. 4D). B16-rhZAG tumors show clear evidence of reactivity with αPEP7 polyclonal anti-tyrosinase antibody in immunoperoxidase assays (red color, FIG. 4F), but their reactivity is decreased relative to B16-V tumors (FIG. 4E). Neither B16-V nor B16-rhZAG tumors react with normal rabbit serum alone (FIG. 4G,H), and αPEP7 is non-reactive with 4T1 breast carcinoma tumors that do not produce melanin, further confirming the specificity of the αPEP7 reagent. To further study the relation between tyrosinase protein levels and tyrosinase enzyme activity, Western blots were also performed using extracts from three different B16-V and B16-rhZAG tumors. Specific bands corresponding to tyrosinase protein were present in all six tumors studied. However the amount of tyrosinase was qualitatively decreased in at least 2 of the 3 B16-rhZAG tumors tested. No reactivity was seen in duplicate blots reacted with control rabbit serum or in lanes containing extracts of 4T1-rhZAG breast cancer tumors that do not express tyrosinase. Thus, ZAG over-expression appears to decrease but does not abrogate the expression of tyrosinase protein in B16 tumors, when examined both immunohistologically and by Western blot.

The almost total lack of tyrosinase activity in B16-rhZAG tumors (FIG. 4D) despite the presence of immunohistologically detectable tyrosinase protein (FIG. 4F) suggested that ZAG may also affect tyrosinase activity by other mechanisms, in addition to affecting levels of tyrosinase protein. To determine whether ZAG could directly affect the activity of tyrosinase protein, frozen sections of B16-V tumors were incubated with varying concentrations of exogenous rhZAG prior to addition of the tyrosinase substrate L-DOPA. Sections incubated with 1-8 mg/ml rhZAG had a 25-50% decrease in color development with L-DOPA. ZAG concentrations less than 1 mg/ml gave no visible inhibition of the L-DOPA reaction. Taken together, the immunohistochemical and L-DOPA studies clearly demonstrate that ZAG decreases melanin synthesis in B16 melanoma cells by post-transcriptional effects on the level and activity of tyrosinase protein.

ZAG Inhibits Melanin Synthesis by Normal Melanocytes

Figure 5A:
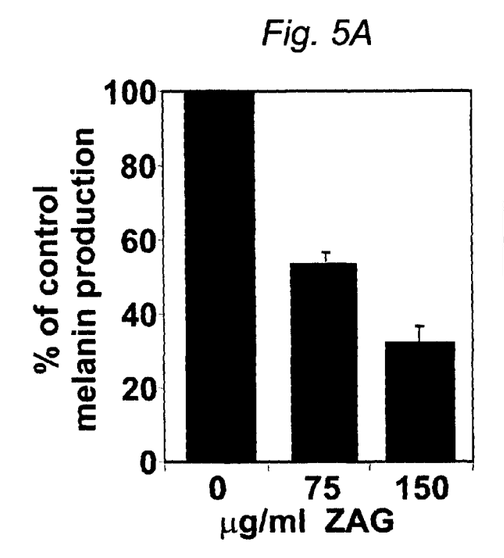
Figure 5B:
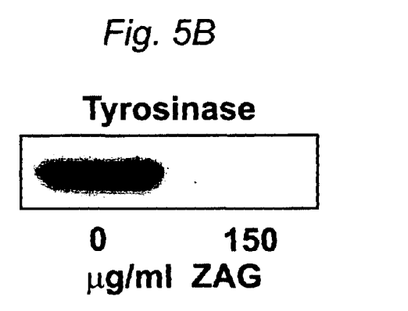
Figure 5C:
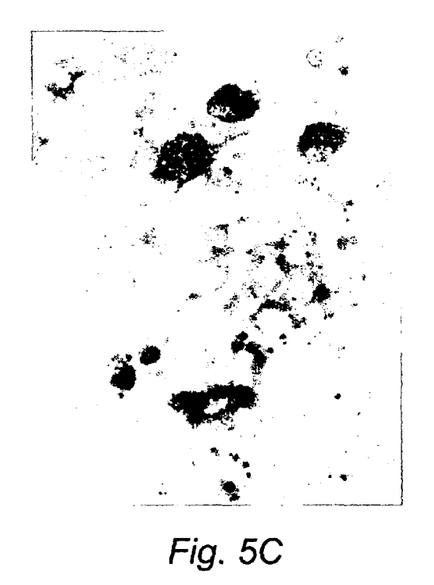
Figure 5D:
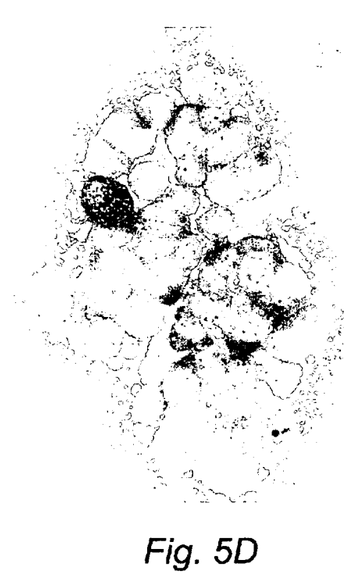

To determine whether ZAG also affects melanin synthesis by normal melanocytes, the melanin content of melan-A primary murine melanocytes treated with varying concentrations of ZAG was determined. As shown in FIG. 5A, ZAG decreased melanin synthesis by melan-A cells in a dose-dependent fashion, with a mean inhibition of 68% at 150 µg/ml exogenous ZAG. The number of heavily melanized cells seen in eosin-stained cytocentrifuge preparations was decreased by ZAG treatment (FIG. 5C, D). Finally, Western blots using αPEP7 anti-tyrosinase Ab (FIG. 5B) demonstrated that 150 µg/ml ZAG markedly decreased levels of tyrosinase protein in melan-A cells, similar to its effect in B16 cells. Thus these studies indicate that ZAG has similar effects on melanin production in both normal and malignant melanocytes.

REFERENCES

Aroca P, Urabe K, Kobayashi T, Tsukamoto K, Hearing V J. Melanin biosynthesis patterns following hormonal stimulation. J Biol Chem 268:25650-25655, 1993

Brysk M M, Lei G, Selvanayagam P, Brysk H, Tyring S K, Arany I. Modulation by interferon-γ of zinc-α2-glycoprotein gene expression in human epithelial cell lines. Anticancer Res. 17:3387-3392, 1997

Brysk M M, Lei G, Rajaraman S, Selvanayagam P, Rassekh C H, Brysk H, Tyring S K, Arany I. Gene expression of zinc-a2-glycoprotein in normal human epidermal and buccal epithelia. In Vivo 11:271-274, 1997b Bundred N J, Miller W R, Walker R A. An immunohistochemical study of the tissue distribution of the breast cyst fluid protein, zinc alpha2-glycoprotein. Histopathol. 11:603-610, 1987.

Burgi W, Schmid K. Preparation and properties of Zn α2-glycoprotein of normal human plasma. J Biol Chem. 236: 1066-1074, 1961

Diez-Itza I, Sanchez L M, Allende M T, Vizoso F, Ruibal A, Lopez-Otin C. Zn-α2-glycoprotein levels in breast cancer cytosols and correlation with clinical, histological, and biochemical parameters. Eur J Cancer 29A: 1256-1260, 1993

Freije J P, Fueyo A, Uria J, Lopez-Otin C. Human Zn-α2-glycoprotein cDNA cloning and expression analysis in benign and malignant breast tissues. FEBS Lett. 290:247-249, 1991

Gordon P R, Mansur C P, Gilchrest B A. Regulation of melanocyte growth, dendricity, and melanization by keratinocyte-derived factors. J. Invest. Dermatol. 92:565-572, 1989

Hale L P, Price D T, Sanchez L M, Demark-Wahnefried W, Madden J F. Zinc alpha-2-glycoprotein is expressed by malignant prostatic epithelium and may serve as a potential serum marker for prostate cancer. Clin. Cancer Res7:846-853, 2001, Hirai K, Hussey H J, Barber M D, Price S A, Tisdale M J. Biological evaluation of a lipid-mobilizing factor isolated from the urine of cancer patients. Cancer Res. 58:2359-2365, 1998

Jimenez M, Tsukamoto K, Hearing V J. Tyrosinases from two different loci are expressed by normal and by transformed melanocytes. J Biol Chem 266:1147-1156, 1991

Jirka M, Blanicky P, Cerna M. The Zn-alpha 2-glycoprotein level in human serum during ontogenesis. Clin. Chim. Acta 56:31-36, 1974

Jirka M, Blanicky P, Srajer J, Zwinger A, Jirasel J E. Human serum Zn-α2-glycoprotein in amniotic fluid. Clin Chim Acta 85:107-110, 1978

Lei G, Arany I, Selvanayagam P, Rajaraman S, Ram S, Brysk H, Tyring S K, Brysk M M. Detection and cloning of epidermal zinc-α2-glycoprotein cDNA and expression in normal human skin and tumors. J. Cell. Biochem. 67:216-222, 1997

Lei G, Brysk H, Arany I, Srinivasan G, Brysk M M. Characterization of zinc-α2-glycoprotein as a cell adhesion molecule that inhibits the proliferation of an oral tumor cell line. J. Cell. Biochem. 75:160-169, 1999

Lipton J M, Catania A. Anti-inflammatory actions of the neuroimmunomodulator α-MSH. Immunol. Today 18:140-145, 1997

Lopez-Boado Y, Diez-Itza I, Tolivia J, Lopez-Otin C. Glucocorticoids and androgens up-regulate the Zn-α2-glycoprotein messenger RNA in human breast cancer cells. Breast Cancer Res Treat. 29:247-258, 1994

Martinez-Esparza M, Jimenez-Cervantes C, Solano F, Lozano J A, Garcia-Borron J C. Mechanisms of melanogenesis inhibition by tumor necrosis factor-α in B16/F10 mouse melanoma cells. Eur J Biochem. 255:139-146, 1998

Martinez-Esparza M, Solano F, Garcia-Borron J C. Independent regulation of tyrosinase by the hypopigmenting cytokines TGFβ1 and TNFα and the melanogenic hormone α-MSH in B16 mouse melanocytes. Cell Molec Biol. 45:991-1000, 1999

Ottaviani E, Franchini A, Franceschi C. Pro-opiomelanocortin-derived peptides, cytokines, and nitric oxide in immune responses and stress: an evolutionary approach. Int Rev Cytol. 170:79-141, 1997

Poortmans J R, Schmid K. The levels of Zn α2-glycoprotein in normal human body fluids and kidney extracts. J. Lab. Clin Med. 71:807-811, 1968

Sanchez L M, Vizoso F, Diez-Itza I, Lopez-Otin C. Identification of the major protein components in breast secretions from women with benign and malignant breast diseases. Cancer Res. 32:95-100, 1992

Sanchez L M, Lopez-Otin C, Bjorkman P J. Biochemical characterization and crystalization of human Zn-α2-glycoprotein, a soluble class I major histocompatibility complex ligand. Proc Natl Acad Sci USA 94:4626-4630, 1997

Sanchez L M, Chirino A J, Bjorkman P J. Crystal structure of human ZAG, a fat-depleting factor related to MHC molecules. Science 283:1914-1919, 1999

Sampson J H, Ashley D M, Archer G E, Fichs H E, Dranoff G, Hale L P, Bigner D D. Characterization of a spontaneous murine astrocytoma and abrogation of its tumorigenicity by cytokine secretion. Neurosurgery 41:1365-1372, 1997

Sheehan D C, Hrapchak B B. Theory and practice of histotechnology, 2nd Edition. Batelle Press, Columbus, Ohio. 1987, pp. 222-224

Swope V B, Abdel-Malek, Kassem L M, Nordlund J J. Interleukins 1α and 6 and tumor necrosis factor-α are paracrine inhibitors of human melanocyte proliferation and melanogenesis. J Invest Dermatol. 96:180-185, 1991

Tada T, Ohkubo I, Niwa M, Sasaki M, Tateyama H, Eimoto T. Immunohistochemical localization of Zn α2-glycoprotein in normal human tissues. J Histochem Cytochem. 39:1221-1226, 1991

Todorov P T, McDevitt T M, Meyer D J, Ueyama H, Ohkubo I, Tisdale M J. Purification and characterization of a tumor lipid-mobilizing factor. Cancer Res. 58:2353-2358, 1998

All documents cited above are hereby incorporated in their entirety by reference.

What is claimed is:

1. A method of inhibiting melanin synthesis in the skin of a patient comprising administering directly to said skin of said patient an amount of ZAG sufficient to effect said inhibition.

2. The method according to claim 1 wherein said patient suffers from hyperpigmentation.

3. The method according to claim 2 wherein said hyperpigmentation results from sun-exposure, inflammation or scarring.

4. The method according to claim 2 wherein said patient suffers from a disorder associated with congenital or acquired proliferation of melanocytes.

* * * * *

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 1
cagatctctg atggccat                                                 18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 2
ggatgacata gactgagc                                                 18

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
tcgtcccgta gacaaaatg                                                19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 4
tgacaagctt cccattctc                                                19

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
tgtctactga acttcggg                                                 18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tctttgagat ccatgccg                                                 18